(12) United States Patent
Morita et al.

(10) Patent No.: US 6,444,213 B1
(45) Date of Patent: Sep. 3, 2002

(54) COSMETICS WITH HYDROFLUOROETHER (HFE)

(75) Inventors: Masamichi Morita; Motonobu Kubo, both of Settsu (JP)

(73) Assignee: Daikin Industries Ltd., Osaka (JP)

(*) Notice: Subject to any disclaimer, the term of this patent is extended or adjusted under 35 U.S.C. 154(b) by 0 days.

(21) Appl. No.: 09/486,367

(22) PCT Filed: Aug. 6, 1998

(86) PCT No.: PCT/JP98/03499

§ 371 (c)(1),
(2), (4) Date: Feb. 18, 2000

(87) PCT Pub. No.: WO99/11225

PCT Pub. Date: Mar. 11, 1999

(30) Foreign Application Priority Data

Aug. 28, 1997 (JP) ............................................. 9-232891

(51) Int. Cl.⁷ ................................................. A61K 7/00
(52) U.S. Cl. .......................... 424/401; 424/63; 424/70.1
(58) Field of Search .......................... 424/401, 63, 70.1

(56) References Cited

U.S. PATENT DOCUMENTS

| | | | |
|---|---|---|---|
| 4,803,067 A | 2/1989 | Brunetta et al. | 424/63 |
| 5,304,334 A | 4/1994 | Lahanas et al. | 252/314 |
| 5,330,681 A | 7/1994 | Brunetta et al. | 252/312 |
| 5,358,719 A | * 10/1994 | Mellul et al. | 424/497 |
| 5,571,858 A | 11/1996 | de La Poterie et al. | 524/462 |
| 5,578,311 A | 11/1996 | Nagatania et al. | 424/401 |
| 5,667,772 A | 9/1997 | Zastrow et al. | 424/18.02 |
| 5,851,539 A | 12/1998 | Mellul et al. | 424/401 |
| 5,925,611 A | 7/1999 | Flynn et al. | 510/412 |
| 6,002,048 A | 12/1999 | Fujii et al. | 568/579 |
| 6,060,626 A | 5/2000 | Fujii et al. | 568/463 |

FOREIGN PATENT DOCUMENTS

| | | |
|---|---|---|
| EP | 1000602 | 5/2000 |
| JP | 62-123107 | 6/1987 |
| JP | 62-223105 | 10/1987 |
| JP | 62249913 | 10/1987 |
| JP | 05000982 A | * 1/1993 |
| JP | 06227942 | 8/1994 |
| JP | 6-2274942 | 8/1994 |
| JP | 07133210 | 5/1995 |
| WO | 96/22356 | 7/1996 |

OTHER PUBLICATIONS

Sigma–Aldrich On–line Catalog, Jul. 16, 1998, Product No. 65139.*
3M News, "3m to Highlight New Cosmetic Technologies at In–Cosmetics USA Show".*
Koenig, T. and Owens, J. "The Role of Hydrofluoroethers in Stratospheric Ozone Protection".*
Jun. 1996 HFE–7100 Product Information Sheet.
Owens et al., "Performance of Hydrofluoroethers in Cleaning Applications," Presented Oct. 1995, International CFC and Halon Alternatives Conference, Washington, D.C.
Pantini et al., "Perfluoropolyethers Status and New Developments" Cosmetics & Toiletries, pp. 71–80, vol. 106 (Oct. 1991).
Seikya et al., "A continuing search for new refrigerants," Chemtech, pp. 44–48 (Dec. 1996).
3M Website, May 22, 1997.
JP–A–62–292713, Dec. 19, 1987, abstract only.
JP–A–63–002916, Jan. 7, 1988, abstract only.

* cited by examiner

Primary Examiner—Jose' G. Dees
Assistant Examiner—Robert M DeWitty
(74) Attorney, Agent, or Firm—Birch, Stewart, Kolasch & Birch, LLP

(57) ABSTRACT

A cosmetic containing at least 1% by weight of hydrofluoroether having a viscosity of less than 5 mPa·s at 25° C., which is represented by the general formula (1):

$$C_nH_mF_l\text{—O—}C_xH_yF_z \tag{1}$$

wherein n is a number of 1 to 12, m is a number of 0 to 25, l is a number of 0 to 11, m+l=2n+1, x is a number of 1 to 12, y is a number of 0 to 25, z is a number of 0 to 11, and y+z=2x+1, provided that m and y are not be simultaneously zero, and l and z are not be simultaneously zero, gives no environment disruption, is highly safe for the skin and improves the feeling in use.

18 Claims, No Drawings

COSMETICS WITH HYDROFLUOROETHER (HFE)

This application is the national phase under 35 U.S.C. §371 of PCT International Application No. PCT/JP98/03499 which has an International filing date of Aug. 6, 1998, which designated the United States of America.

FIELD OF THE INVENTION

The present invention relates to a cosmetic comprising hydrofluoroether (abbreviated hereinafter into "HFE") having a viscosity of less than 5 mPa·s at 25° C. which is a fluorine-containing solvent causing no environmental disruption and being highly safe for the skin. The HFE is characterized by these properties as well as by high solubility in fluorine-containing oil having a viscosity of at least 5 mPa·s at 25° C. and high dispersibility in a fluorine compound-treated powder.

RELATED ART

In recent years, cosmetics incorporating volatile solvents such as isoparaffin and cyclic silicone are frequently used. These volatile solvents have the advantage that upon application there is a refreshing feeling and their solubility is high, and their use can easily improve the feeling of cosmetics in use and increase the functionality thereof. However, isoparaffin and cyclic silicone severely irritate the skin and have the problem of their adverse influence on the environment after volatilization.

Fluorocarbons such as perfluorohexane, chlorofluorocarbon (CFC) and hydrochlorofluorocarbon (HCFC) have also been examined as substitutes for these solvents. Because the ozone depletion coefficient and warming coefficient of these solvents are high, there is the disadvantage that they are highly dangerous owing to environmental disruption.

SUMMARY OF THE INVENTION

As a result of the intense study for solving the problem described above, the present inventors found that a partially fluorinated fluorine-containing solvent, the HFE, is highly safe for the skin and has less or no influence on the environment. In addition to the properties described above, the HFE has high solubility in a fluorine-containing—oil used frequently in recent cosmetics and high dispersibility in fluorine compound-treated powders, thus easily permitting improvements in the feeling of cosmetics upon use, and giving a high functionality.

The present invention provides a cosmetic comprising at least 1% by weight of the HFE having a viscosity of less than 5 mPa·s at 25° C., represented by the general formula (1):

$$C_nH_mF_l\text{—}O\text{—}C_xH_yF_z \tag{1}$$

wherein n is a number of 1 to 12, m is a number of 0 to 25, l is a number of 0 to 11, m+l=2n+1, x is a number of 1 to 12, y is a number of 0 to 25, z is a number of 0 to 11, and y+z=2x+1, provided that m and y are not be simultaneously zero, and l and z are not be simultaneously zero.

The cosmetic of the present invention serve as a finishing cosmetic such as foundation, face powder, cheek color and eye color, a fundamental cosmetic such as face lotion, milky lotion, cream and sunscreen milky lotion, and hair-caring products such as rinse and conditioner, and lipstick overcoat.

DETAILED DESCRIPTION OF THE INVENTION

Preferably, the HFE is of the general formula (1'):

$$C_nF_{2n+1}\text{—}O\text{—}C_xH_{2x+1} \tag{1'}$$

wherein n is a number of 1 to 12, and x is a number of 1 to 12.

In the formulas (1) and (1'), n may be e.g. 1 to 10, particularly 1 to 6, and x may be e.g. 1 to 10, particularly 1 to 6.

Specific examples of the HFE include:

$$C_4F_9OCH_3,\ C_4F_9OC_2H_5,\ C_4F_9OC_3H_7,\ C_5F_{11}OC_2H_5,\ C_3F_7OC_4H_9$$
and $C_4F_9OC_4H_9$.

The HFE may be incorporated alone into the cosmetic or may be used as a mixture of at least two types. The amount of the HFE is at least 1% by weight, for example 1 to 99.9% by weight, preferably 5 to 99% by weight, particularly 10 to 99% by weight, based on the cosmetic. The cosmetic comprising the HFE can be produced in a conventional manner.

The HFE is advantageously superior in the ability to dissolve a fluorine-containing oil having a viscosity of at least 5 mPa·s at 25° C. By virtue of this advantage, the cosmetic having the advantage never achieved can be produced. It is preferable that at least 1% by weight of the fluorine-containing oil and at least 5% by weight of the HFE are contained in the cosmetic. For example, the amount of the fluorine-containing oil is preferably 1 to 90% by weight, particularly 5 to 50% by weight, for example 5 to 20% by weight, based on the cosmetic. For example, a weight ratio of the fluorine-containing oil to the HFE may be in the range of from 1:100 to 1:5, preferably from 1:90 to 1:10.

The fluorine-containing oil having a viscosity of at least 5 mPa·s may be, for example, a perfluoropolyether, or a fluorine-based oil represented by the general formula (2):

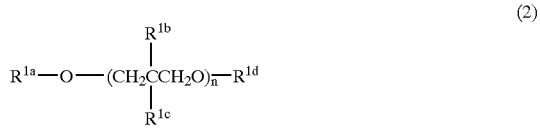

wherein $R^{1a}$ and $R^{1d}$ are each a hydrogen atom or a partially or completely fluorinated aliphatic group having 1 to 20 carbon atoms; $R^{1b}$ and $R^{1c}$ are each a hydrogen atom, or an aliphatic group having 1 to 20 carbon atoms, or a partially or completely fluorinated aliphatic group having 1 to 20 carbon atoms, with the proviso that at least one of $R^{1a}$ to $R^{1d}$ is a partially or completely fluorinated aliphatic group having 1 to 20 carbon atoms; and n is a number of 1 to 20, or a fluorine-based oil represented by the general formula (3):

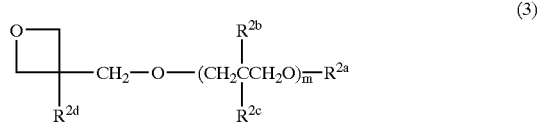

wherein $R^{2a}$ is a hydrogen atom or a partially or completely fluorinated aliphatic group having 1 to 20 carbon atoms; $R^{2b}$, $R^{2c}$ and $R^{2d}$ are each an aliphatic group having 1 to 20 carbon atoms or a partially or completely fluorinated aliphatic group having 1 to 20 carbon atoms, with the proviso that at least one of $R^{2a}$ to $R^{2d}$ is a partially or completely fluorinated aliphatic group having 1 to 20 carbon atoms; and m is a number of 1 to 20.

The viscosity of the fluorine-containing oil is e.g. at least 5 mPa·s, particularly 10 to 10,000 mPa·s. The viscosity of the fluorine oil (and the HFE) was measured by a Brookfield type viscometer or a capillary tube viscometer.

Specific examples of the perfluoropolyether include:

$F(CF(CF_3)CF_2O)_nCF_2CF_3$ (KRYTOX manufactured by Du Pont Co.);

$CF_3O(CF(CF_3)CF_2O)_n(CF_2O)_mCF_3$ (FOMBLIN Y manufactured by Montefluos Ltd.);

$CF_3O(CF_2CF_2O)_n(CF_2O)_mCF_3$ (FOMBLIN Z manufactured by Montefluos Ltd.); and $F(CF_2CF_2CF_2O)_nCF_2CF_3$ (DEMNUM manufactured by Daikin Industries, Ltd.).

A number average molecular weight of the perfluoropolyether (as determined by $^{19}$F-NMR) is preferably in the range of 1,000 to 10,000.

In the general formulas (2) and (3), if $R^{1a}$, $R^{1b}$, $R^{1c}$, $R^{1d}$, $R^{2a}$, $R^{2b}$, $R^{2c}$ and $R^{2d}$ are partially or fully fluorinated aliphatic groups, these may contain an oxygen atom or an unsaturated bond. The partially fluorinated aliphatic group may be e.g. $R^{10}OCH_2$ group ($R^{10}$ is a partially or fully fluorinated aliphatic group (e.g. alkyl group)). Examples of the partially or fully fluorinated aliphatic group are as follows:

—$CFH_2$
—$CF_2H$
—$CF_3$
—$CF_2CF_2H$,
—$CF_2CF_3$,
—$CF_2CFHCF_3$,
—$CF_2CH_3$,
—$CF_2CFH_2$,
—$(CF_3)_2CH_3$,
—$CF_2CH(CF_3)_2$,
—$C(CF_3)_2CF_2H$,
—$C(CH_3)FCF_2CF_2CF_3$,
—$CH_2CF_2CH_2OH$

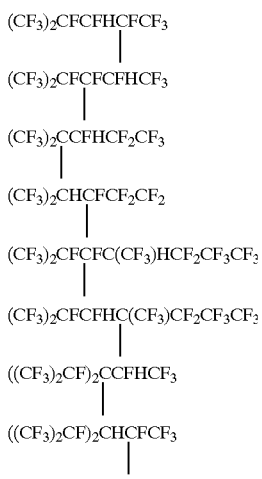

—$CH_2CF_2COOR^{11}$ ($R^{11}$ is a $C_1$ to $C_{10}$ aliphatic group).

If $R^{1b}$, $R^{1c}$, $R^{2b}$, $R^{2c}$ and $R^{2d}$ are a $C_1$ to $C_{20}$ aliphatic group, these may have an oxygen atom. Examples of the $C_1$ to $C_{20}$ aliphatic group include an alkyl group such as methyl, ethyl, n-propyl, isopropyl, n-butyl, isobutyl, sec-butyl and t-butyl as well as a hydroxyalkyl group such as hydroxymethyl and 2-hydroxyethyl (—$CH_2CH_2OH$).

$R^{1b}$, $R^{1c}$, $R^{2b}$ and $R^{2c}$ in the repeating unit may be the same or different.

The number of carbon atoms in each of $R^{1a}$ to $R^{1d}$ and $R^{2a}$ to $R^{2d}$ is from 1 to 10, particularly from 2 to 4.

Specific examples of the fluorine-based oil represented by the general formula (2) are as follows:

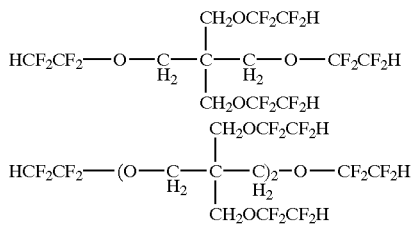

Specific examples of the fluorine-based oil represented by the general formula (3) are as follows:

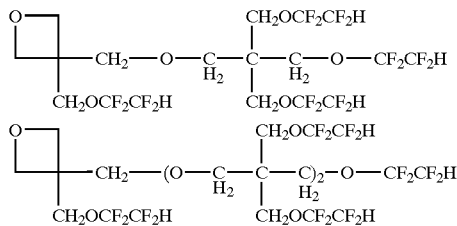

The fluorine-containing oil may be a mixture of at least two types. For example, a mixture consisting of the fluorine-based oils of the general formulas (2) and (3) at a weight ratio of from 5:95 to 95:5, for example 20:80 to 80:20, may be used as the fluorine-containing oil.

The HFE of the present invention is advantageously superior in the ability to disperse a fluorine compound treated powder. By use of this advantage, the cosmetic having the characteristics never achieved in the past can be produced as well.

It is preferable that at least 1% by weight, based on the cosmetic, of the fluorine compound-treated powder and at least 5% by weight, based on the cosmetic, of the HFE are contained. For example, the amount of the fluorine compound-treated powder in the cosmetic is preferably 1 to 90% by weight, particularly 5 to 50% by weight, for example 5 to 20% by weight, based on the cosmetic. For example, the weight ratio of the fluorine compound-treated powder to the HFE may be in the range of from 1:100 to 1:5, preferably 1:90 to 1:10.

The fluorine compound-treated powder may be a powder which is surface-treated with a fluorine-containing phosphate ester represented, for example, by the general formula (4):

$$[Rf—A—O]_nPO(OM)_{3-n} \qquad (4)$$

wherein Rf represents a $C_6$ to $C_6$ polyfluoroalkyl group or perfluoropolyether group, "A" represents a $C_1$ to $C_4$ alkylene group,

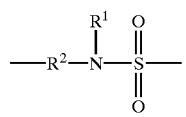

(wherein $R^1$ is a $C_1$ to $C_4$ alkyl group and $R^2$ is a $C_1$ to $C_4$ alkylene group), or

wherein "M" represents a hydrogen atom, a metal atom, ammonium or substituted ammonium, and n is a number of 1 to 3.

A base powder to be treated includes inorganic powder such as talc, kaolin, mica, mica titanium, titanium oxide, iron oxide, magnesium oxide, zinc monoxide, zinc dioxide, heavy or light calcium carbonate, dibasic calcium phosphate, aluminum hydroxide, barium sulfate, silica, alumina, silica gel, carbon black, antimony oxide, magnesium silicate aluminate and magnesium metasilicate aluminate, as well as an organic powder such as protein powder, fish scale, metallic soap, polyvinyl chloride, nylon-12, microcrystalline fiber powder and tar pigment.

The base powder may be treated with 1 to 10% by weight, relative to the base powder, of the fluorine-containing phosphate ester. The surface treatment may be generally surface coating.

In the present invention, suitable chemicals for modifying the feeling in use may be also employed in the step of surface treatment. Examples of the chemicals for modifying the feeling of the cosmetic powder in use include lecithin, N-mono long-chain acyl basic amino acids, silicone, chitosan, collagen and wax.

When the fluorine compound-treated powder is incorporated into the cosmetic, at least two types of the powders may be mixed.

Furthermore, the cosmetic may simultaneously comprise three ingredients, that is, HFE, the fluorine-containing oil and the fluorine compound-treated powder. Based on the cosmetic comprising three ingredients, the HFE may be contained in an amount of 5 to 99% by weight, preferably 10 to 90% by weight, the fluorine-containing oil may be contained in an amount of 0.5 to 90% by weight, preferably 5 to 50% by weight, and the fluorine compound-treated powder may be contained in an amount of 0.5 to 90% by weight, preferably 5 to 50% by weight.

The cosmetic of the present invention may contain solid or semi-solid oils such as Vaseline, lanolin, ceresin, microcrystalline wax, carnauba wax, candelilla wax, higher aliphatic acids and higher alcohols; liquid oils such as squalane, liquid paraffin, ester oils, diglycerides, triglycerides and silicone oil; fluorine-containing oils such as perfluoropolyether, perfluorodecalin and perfluoroctane; water- and oil-soluble polymers, surface active agents, coloring agents such as organic dyestuffs, ethanol, preservatives, antioxidants, pigments, thickening agents, pH adjusters, perfumes, UV absorbers, humectants, blood stream promoters, coolants, sweat regulators, germicides, skin activators etc.

PREFERRED EMBODIMENT OF THE INVENTION

The examples of the present invention is described specifically, but this description does not limit the present invention.

EXAMPLE 1

50% by weight of a perfluoropolyether (FOMBLIN HC/04 manufactured by Audimont) (viscosity at 25° C.: 70 mPa·s) was mixed with 50% by weight of $C_4F_9OCH_3$ (HFE A) (viscosity at 25° C.: 0.6 mPa·s) under stirring to give a solution. Thereafter, a very small amount of a perfume was added to give a non-aqueous lotion. This non-aqueous lotion was felt very smooth in use. After the lotion was applied onto the skin, the HFE A evaporated rapidly and a uniform coating of the perfluoropolyether maintained the skin moisture.

EXAMPLE 2

A non-aqueous lotion was obtained in the same manner as in Example 1 except that the perfluoropolyether was replaced by a mixture (A/B=8/2 by weight) of the fluorine-containing oil (viscosity at 25° C.: 35 mPa·s) represented by chemical formula A:

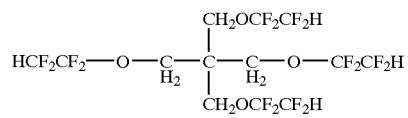

and the fluorine-containing oil (viscosity at 25° C.: 40 mPa·s) represented by chemical formula B:

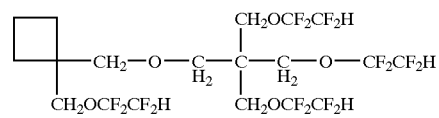

This non-aqueous location had the same properties as in Example 1.

EXAMPLE 3

A non-aqueous lotion was obtained in the same manner as in Example 1 except that the perfluoropolyether was replaced by a mixture (C/D=7/3 by weight) of the fluorine-containing oil (viscosity at 25° C.: 350 mPa·s) represented by chemical formula C:

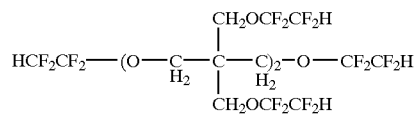

and the fluorine-containing oil (viscosity at 25° C.: 400 mPa·s) represented by chemical formula D:

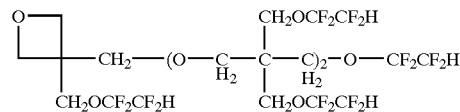

This non-aqueous location had the same properties as in Example 1.

In the Examples below, the mixture powder (a mixture of fluorine compound-treated powders) shown in Table 1 was used to produce a cosmetic. The fluorine compound-treated powder was prepared by treating a powder with 5% by weight of perfluoroalkyl ethyl phosphate ester diethanol amine salt $((C_9F_{19}CH_2CH_2O)_nP(=O)[ONH_2(CH_2CH_2OH)_2]_{3-n}$ (average of n=1.8)).

TABLE 1

Formulation of the Mixture Powder

| Starting Materials | % by weight |
|---|---|
| (1) fluorine compound-treated titanium oxide | 8.0 |
| (2) fluorine compound-treated yellow iron oxide | 0.9 |
| (3) fluorine compound-treated red iron oxide | 0.3 |
| (4) fluorine compound-treated black iron oxide | 0.3 |
| (5) fluorine compound-treated talc | 36.1 |
| (6) fluorine compound-treated sericite | 50.6 |
| (7) fluorine compound-treated mica | 3.8 |

EXAMPLE 4

The powder ingredients in the formulation shown in Table 2 were mixed and ground with an atomizer and then transferred to a Henschel mixer. Then FOMBLIN HC/04 was added thereto, and the mixture was uniformly mixed. The mixture was dispersed in $C_4H_9OC_2H_5$ (HFE B) (viscosity at 25° C.: 0.7 mPa·s) to give a solvent dispersion-type foundation. This solvent dispersion-type foundation was felt very smooth in use. After this foundation was applied onto the skin, the HFE B evaporated rapidly, and the resulting uniform coating maintained the skin moisture.

TABLE 2

Non-Aqueous Dispersion-Type Foundation

| Starting Materials | Blending Amount (% by weight) |
|---|---|
| (1) mixture powder (Table 1) | 10 |
| (2) perfluoropolyether (FOMBLIN HC/04) | 10 |
| (3) HFE B ($C_4F_9OC_2H_5$) | 80 |

EXAMPLE 5

The ingredients (1) to (8) in the formulation shown in Table 3 were mixed and ground in a colloid mill. After this mixture was heated at 80° C., the ingredients (9) to (13) which had been heated and mixed at 80° C. were added thereto and emulsified uniformly in a homomixer. The ingredient (14) was added to this emulsion, further emulsified uniformly in a homomixer, and cooled to room temperature to give a liquid foundation. This liquid foundation was felt very smooth in use.

TABLE 3

Liquid Foundation

| Starting Materials | Blending Amount (% by weight) |
|---|---|
| (1) 1,3-butylene glycol | 10.00 |
| (2) carboxymethyl cellulose | 0.20 |
| (3) aluminum magnesium silicate | 0.20 |
| (4) mixture powder (Table 1) | 14.00 |
| (5) purified water | 50.75 |
| (6) sodium N-stearoyl-L-glutamate | 0.75 |
| (7) potassium hydroxide | 0.40 |
| (8) p-oxybenzoate | 0.20 |
| (9) glyceryl trioctanoate | 5.00 |
| (10) diisostearyl malate | 3.00 |
| (11) stearic acid | 3.00 |

TABLE 3-continued

Liquid Foundation

| Starting Materials | Blending Amount (% by weight) |
|---|---|
| (12) glyceride monostearate | 1.50 |
| (13) cethanol | 1.00 |
| (14) HFE D ($C_4F_9OC_4H_9$) | 10.00 |

EXAMPLE 6

The fluorine compound-treated zinc oxide as the ingredient (3) shown in Table 4 was a product prepared by treating zinc oxide with 7% by weight, based on zinc oxide, of a perfluoroalkyl ethyl phosphate ester diethanolamine salt (the same as used in Example 3).

In the formulation shown in Table 4, the ingredients (1) and (2) were mixed and dissolved at room temperature, and the ingredient (3) was added thereto and dispersed with a disper. The ingredients (4) to (9) were added thereto under stirring and emulsified with a homomixer to give a sunscreen emulsion. This sunscreen emulsion was felt very smooth in use. After this emulsion was applied onto the skin, the HFE A evaporated rapidly, and the resulting uniform coating maintained the skin moisture.

TABLE 4

Sunscreen Emulsion

| Starting Materials | Blending Amount % by weight |
|---|---|
| (1) HFE A ($C_4F_2OCH_3$) | 40 |
| (2) fluorine-containing oil (the same as used in Example 2) | 10 |
| (3) fluorine compound-treated zinc oxide | 5 |
| (4) dimethylpolysiloxane-polyoxyalkylene copolymer | 3 |
| (5) glycerin | 2 |
| (6) ethanol | 5 |
| (7) water | 32.9 |
| (8) octyl methoxycinnamate | 2 |
| (9) perfume | 0.1 |

EXAMPLE 7

A set lotion was produced using the formulation shown in Table 5. After the ingredients (4) to (7) were dissolved, the ingredients (1) to (3) were added, moistened, and dissolved. Further, the ingredient (8) was added thereto slowly under stirring to give a set lotion. This set lotion was felt very smooth in use.

TABLE 5

Set Lotion

| Starting Materials | Blending Amount (% by weight) |
|---|---|
| (1) polyvinyl pyrrolidone | 5 |
| (2) polyoxyethylene (20) oleylether | 5 |
| (3) 1,3-butylene glycol | 10 |
| (4) HFE B ($C_4F_2OC_2H_5$) | 5 |
| (5) p-oxybenzoate ester | 0.1 |
| (6) colorant | Trace amount |
| (7) perfume | 0.5 |
| (8) purified water | Adjusted to 100 |

EFFECT OF THE INVENTION

The HFE causing no environmental disruption and being highly safe for the skin is incorporated into the cosmetic, thereby increasing the solubility in the fluorine-containing oil and dispersibility in the fluorine compound-treated powder. The feeling of the cosmetic in use can be improved and the functionality of the cosmetic can be increased.

What is claimed is:

1. A cosmetic comprising
at least one compound or composition selected from the group consisting of petrolatum, lanolin, ceresin, microcrystalline wax, carnauba wax, candelilla wax, higher aliphatic acids, higher alcohols, squalane, liquid paraffin, ester oils, diglycerides, triglycerides, silicone oil, perfluoropolyether, perfluorodecalin, perfluoroctane, water-soluble polymers, oil-soluble polymers, surface active agents, coloring agents, ethanol, preservatives, antioxidants, pigments, thickening agents, pH adjusters, perfumes, UV absorbers, humectants, blood stream promoters, coolants, sweat regulators, germicides and skin activators; and
at least 1% by weight of a hydrofluoroether, wherein the hydrofluoroether has a viscosity of less than 5 mPa·s at 25° C. and is represented by the general formula (1):

(1)

wherein n is a number of 1 to 6, and x is a number of 1 to 6.

2. The cosmetic according to claim 1, which comprises:
at least 1% by weight of a fluorine-containing oil having a viscosity of at least 5 mPa·s at 25° C.; and at least 5% by weight of hydrofluoroether.

3. The cosmetic according to claim 2, wherein the fluorine-containing oil is a perfluoropolyether, a fluorine-based oil represented by the general formula (2):

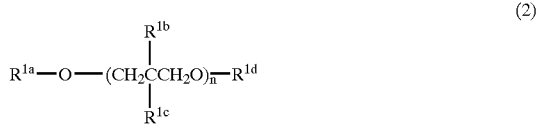

(2)

wherein $R^{1a}$ and $R^{1d}$ are each a hydrogen atom or a partially or completely fluorinated aliphatic group having 1 to 20 carbon atoms; $R^{1b}$ and $R^{1c}$ are each a hydrogen atom, or an aliphatic group having 1 to 20 carbon atoms, or a partially or completely fluorinated aliphatic group having 1 to 20 carbon atoms, with the proviso that at least one of $R^{1a}$ to $R^{1d}$ is a partially or completely fluorinated aliphatic group having 1 to 20 carbon atoms; and n is a number of 1 to 20, or a fluorine-based oil represented by the general formula (3)

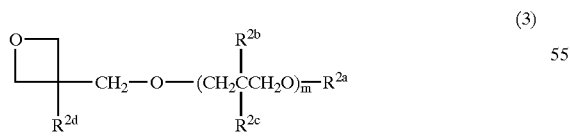

(3)

wherein $R^{2a}$ is a hydrogen atom or a partially or completely fluorinated aliphatic group having 1 to 20 carbon atoms; $R^{2b}$, $R^{2c}$ and $R^{2d}$ are each an aliphatic group having 1 to 20 carbon atoms or a partially or completely fluorinated aliphatic group having 1 to 20 carbon atoms, with the proviso that at least one of $R^{2a}$ to $R^{2d}$ is a partially or completely fluorinated aliphatic group having 1 to 20 carbon atoms, and m is a number of 1 to 20.

4. The cosmetic according to claim 1, which comprises at least 1% by weight of a fluorine compound-treated powder and at least 5% by weight of the hydrofluoroether.

5. The cosmetic according to claim 4, wherein the fluorine compound-treated powder is a powder surface-treated with a fluorine-containing phosphate ester represented by the general formula (4):

(4)

wherein Rf represents a $C_6$ to $C_{16}$ polyfluoroalkyl group or perfluoropolyether group, A represents a $C_1$ to $C_4$ alkylene group,

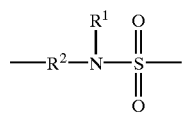

(and $R^1$ is a $C_1$ to $C_4$ alkyl group and $R^2$ is a $C_1$ to $C_4$ alkylene group), or

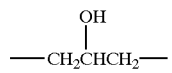

wherein M represents a hydrogen atom, a metal atom, ammonium or substituted ammonium, and n is a number of 1 to 3.

6. A finishing cosmetic, a fundamental cosmetic, a hair-care product, or a lipstick overcoat comprising the cosmetic of claim 1.

7. The cosmetic according to claim 1, further comprising a compound or composition selected from the group consisting of lecithin, N-mono long-chain acyl basic amino acids, silicone, chitosan, collagen and wax.

8. The cosmetic according to claim 3, wherein said perfluoropolyether has a number average molecular weight of 1,000 to 10,000, and is selected from the group consisting of
$F(CF(CF_3)CF_2O)_nCF_2CF_3$, $CF_3O(CF(CF_3)CF_2O)_n(CF_2O)_mCF_3$, $CF_3O(CF_2CF_2O)_n(CF_2O)_mCF_3$, and $F(CF_2CF_2CF_2O)_nCF_2CF_3$.

9. The cosmetic according to claim 3, wherein said fluorine-based oil of formula (2) is

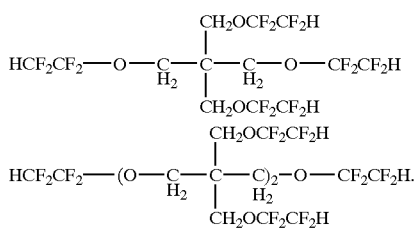

10. The cosmetic according to claim 3, wherein said fluorine-based oil of formula (3) is

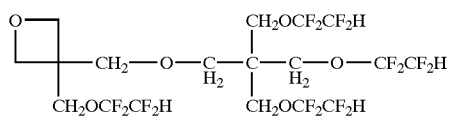

-continued

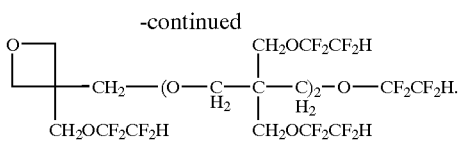

11. The cosmetic according to claim 4 or 5, wherein said fluorine compound-treated powder is in the amount of 5 to 50% by weight.

12. The cosmetic according to claim 4 or 5, wherein the weight ratio of the fluorine compound-treated powder to the hydrofluoroether is from 1:100 to 1:5.

13. The cosmetic according to claim 5, wherein said powder to be surface-treated is selected from the group consisting of talc, kaolin, mica, mica titanium, titanium oxide, iron oxide, magnesium oxide, zinc monoxide, zinc dioxide, heavy calcium carbonate, light calcium carbonate, dibasic calcium phosphate, aluminum hydroxide, barium sulfate, silica, alumina, silica gel, carbon black, antimony oxide, magnesium silicate aluminate and magnesium meta-silicate aluminate, protein powder, fish scale, metallic soap, polyvinyl chloride, nylon-12, microcrystalline fiber powder and tar pigment.

14. The cosmetic according to claim 4 or 5, wherein said cosmetic comprises more than one type of said fluorine compound-treated powder.

15. A cosmetic comprising:
a) at least one compound or composition selected from the group consisting of petrolatum, lanolin, ceresin, microcrystalline wax, carnauba wax, candelilla wax, higher aliphatic acids, higher alcohols, squalane, liquid paraffin, ester oils, diglycerides, triglycerides, silicone oil, perfluoropolyether, perfluorodecalin, perfluoroctane, water-soluble polymers, oil-soluble polymers, surface active agents, coloring agents, ethanol, preservatives, antioxidants, pigments, thickening agents, pH adjusters, perfumes, UV absorbers, humectants, blood stream promoters, coolants, sweat regulators, germicides and skin activators;
b) at least 5% by weight of a hydrofluoroether, wherein the hydrofluoroether has a viscosity of less than 5 mPa·s at 25° C. and is represented by the general formula (1):

$$C_nF_{2n+1}\text{—}O\text{—}C_xH_{2x+1} \quad (1)$$

wherein n is a number of 1 to 6, and x is a number of 1 to 6;
c) at least 0.5% by weight of a fluorine-containing oil; and
d) at least 1% by weight of a fluorine compound-treated powder.

16. The cosmetic according to claim 15, wherein said cosmetic comprises:
10% to 90% by weight of said hydrofluoroether;
5% to 50% by weight of said fluorine-containing oil; and
5% to 50% by weight of said fluorine compound-treated powder.

17. The cosmetic according to claim 16, wherein said fluorine-containing oil is
a perfluoropolyether;
a fluorine-based oil represented by the general formula (2):

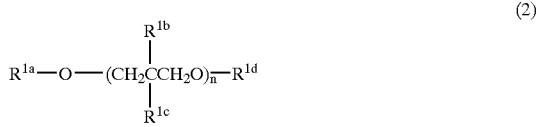

wherein $R^{1a}$ and $R^{1d}$ are each a hydrogen atom or a partially or completely fluorinated aliphatic group having 1 to 20 carbon atoms, $R^{1b}$ and $R^{1c}$ are each a hydrogen atom, or an aliphatic group having 1 to 20 carbon atoms, or a partially or completely fluorinated aliphatic group having 1 to 20 carbon atoms, with the proviso that at least one of $R^{1a}$ to $R^{1d}$ is a partially or completely fluorinated aliphatic group having 1 to 20 carbon atoms, and n is a number of 1 to 20; or
a fluorine-based oil represented by the general formula (3):

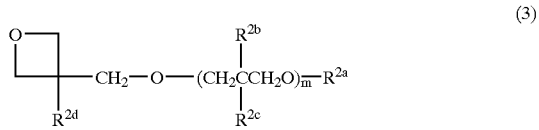

wherein $R^{2a}$ is a hydrogen atom or a partially or completely fluorinated aliphatic group having 1 to 20 carbon atoms, $R^{2b}$, $R^{2c}$ and $R^{2d}$ are each an aliphatic group having 1 to 20 carbon atoms or a partially or completely fluorinated aliphatic group having 1 to 20 carbon atoms, with the proviso that at least one of $R^{2a}$ to $R^{2d}$ is a partially or completely fluorinated aliphatic group having 1 to 20 carbon atoms, and m is a number of 1 to 20.

18. The cosmetic of claim 1, which further contains water.

* * * * *

UNITED STATES PATENT AND TRADEMARK OFFICE
CERTIFICATE OF CORRECTION

PATENT NO.     : 6,444,213 B1  
DATED          : September 3, 2002  
INVENTOR(S)    : Masamichi Morita et al.

It is certified that error appears in the above-identified patent and that said Letters Patent is hereby corrected as shown below:

<u>Title page,</u>  
Item [86], please change the § 371 (c)(1),(2),(4) Date from "Feb. 18, 2000" to -- Feb. 28, 2000 --.

Signed and Sealed this

Twelfth Day of August, 2003

JAMES E. ROGAN  
*Director of the United States Patent and Trademark Office*